(12) United States Patent
Palepu

(10) Patent No.: US 8,912,228 B2
(45) Date of Patent: *Dec. 16, 2014

(54) DOCETAXEL FORMULATIONS WITH LIPOIC ACID

(75) Inventor: Nageswara R. Palepu, Southampton, PA (US)

(73) Assignee: Scidose LLC, Amherst, MA (US)

( * ) Notice: Subject to any disclaimer, the term of this patent is extended or adjusted under 35 U.S.C. 154(b) by 112 days.

This patent is subject to a terminal disclaimer.

(21) Appl. No.: 13/207,339

(22) Filed: Aug. 10, 2011

(65) Prior Publication Data

US 2012/0129922 A1    May 24, 2012

Related U.S. Application Data

(63) Continuation-in-part of application No. 12/721,564, filed on Mar. 11, 2010, now Pat. No. 8,746,310, which is a continuation-in-part of application No. 12/589,145, filed on Oct. 19, 2009, now Pat. No. 8,541,465.

(51) Int. Cl.
| | |
|---|---|
| A61K 31/337 | (2006.01) |
| A61K 31/385 | (2006.01) |
| A61K 9/00 | (2006.01) |
| A61K 47/10 | (2006.01) |
| A61K 47/14 | (2006.01) |
| A61K 47/44 | (2006.01) |
| A61K 47/22 | (2006.01) |
| A61K 9/08 | (2006.01) |
| A61K 47/12 | (2006.01) |

(52) U.S. Cl.
CPC ............. *A61K 9/08* (2013.01); *A61K 9/0019* (2013.01); *A61K 31/385* (2013.01); *A61K 47/10* (2013.01); *A61K 47/14* (2013.01); *A61K 47/44* (2013.01); *A61K 47/22* (2013.01); *A61K 31/337* (2013.01); *A61K 47/12* (2013.01)
USPC ........................................................ 514/449

(58) Field of Classification Search
None
See application file for complete search history.

(56) References Cited

U.S. PATENT DOCUMENTS

| | | |
|---|---|---|
| 4,814,470 A | 3/1989 | Colin et al. |
| 5,403,858 A | 4/1995 | Bastard et al. |
| 5,438,072 A | 8/1995 | Bobee et al. |
| 5,698,582 A | 12/1997 | Bastart et al. |
| 5,714,512 A | 2/1998 | Bastart et al. |
| 5,750,561 A | 5/1998 | Bastart et al. |
| 5,968,972 A | 10/1999 | Broder et al. |
| 6,071,952 A | 6/2000 | Owens et al. |
| 6,136,846 A | 10/2000 | Rubinfeld et al. |
| 6,153,644 A | 11/2000 | Owens et al. |
| 6,245,805 B1 | 6/2001 | Broder et al. |
| 6,319,943 B1 | 11/2001 | Joshi et al. |
| 6,395,770 B1 | 5/2002 | Broder et al. |
| 6,458,373 B1 | 10/2002 | Lambert et al. |
| 6,479,540 B1 | 11/2002 | Constantinides et al. |
| 6,509,370 B1 | 1/2003 | Joshi-Hangal et al. |
| 6,531,139 B1 | 3/2003 | Gao et al. |
| 6,610,735 B2 | 8/2003 | Broder et al. |
| 6,660,286 B1 | 12/2003 | Lambert et al. |
| 6,667,048 B1 | 12/2003 | Lambert et al. |
| 6,727,280 B2 | 4/2004 | Palepu et al. |
| 6,730,698 B2 | 5/2004 | Broder et al. |
| 6,818,615 B2 | 11/2004 | Broder et al. |
| 6,936,583 B2 | 8/2005 | Broder et al. |
| 6,964,946 B1 | 11/2005 | Gutierrez-Rocca et al. |
| 6,979,456 B1 | 12/2005 | Parikh et al. |
| 6,982,282 B2 | 1/2006 | Lambert et al. |
| 7,030,155 B2 | 4/2006 | Lambert et al. |
| 7,041,640 B2 | 5/2006 | Broder et al. |
| 7,115,565 B2 | 10/2006 | Gao et al. |
| 7,223,770 B2 | 5/2007 | Zhang et al. |
| 7,618,975 B2 | 11/2009 | Cai et al. |
| 7,772,274 B1 | 8/2010 | Palepu |
| 8,476,310 B2 * | 7/2013 | Palepu .......................... 514/449 |
| 8,541,465 B2 * | 9/2013 | Palepu .......................... 514/449 |
| 2002/0049158 A1 | 4/2002 | Woo et al. |
| 2002/0102280 A1 | 8/2002 | Anderson |
| 2002/0103254 A1 * | 8/2002 | Joshi-Hangal et al. ....... 514/449 |
| 2002/0156125 A1 | 10/2002 | Broder et al. |
| 2003/0027858 A1 | 2/2003 | Lambert et al. |
| 2003/0087954 A1 | 5/2003 | Palepu et al. |

(Continued)

FOREIGN PATENT DOCUMENTS

| | | |
|---|---|---|
| EP | 1618879 | 1/2006 |
| KR | 10-2010-0018741 | 2/2010 |

(Continued)

OTHER PUBLICATIONS

TAXOTERE® Prescribing Information, Nov. 2008.

(Continued)

*Primary Examiner* — James D Anderson
(74) *Attorney, Agent, or Firm* — Frommer Lawrence & Haug LLP

(57) ABSTRACT

Pharmaceutical formulations comprising docetaxel or a pharmaceutically acceptable salt thereof, one or more solubilizers, α-lipoic acid, TPGS, one or more hydrotropes, and optionally one or more agents having a $pK_a$ of about 3 to about 6. The pharmaceutical formulations are stable and substantially free of excipients that can cause severe side effects and maintains chemical stability during storage. The pharmaceutical formulations are ready to be combined with an infusion solution for administration to patients in need thereof. Methods of treating patients in need thereof comprise administering the pharmaceutical formulations combined with an infusion solution.

20 Claims, No Drawings

(56) References Cited

U.S. PATENT DOCUMENTS

| | | |
|---|---|---|
| 2003/0105156 A1 | 6/2003 | Palepu et al. |
| 2003/0109575 A1 | 6/2003 | Lambert et al. |
| 2003/0147959 A1 | 8/2003 | Lambert et al. |
| 2003/0170279 A1 | 9/2003 | Lambert et al. |
| 2004/0022820 A1 | 2/2004 | Anderson |
| 2004/0053993 A1 | 3/2004 | Constantinides et al. |
| 2004/0127551 A1 | 7/2004 | Zhang et al. |
| 2004/0202712 A1 | 10/2004 | Lambert et al. |
| 2005/0004002 A1 | 1/2005 | Desai et al. |
| 2005/0119340 A1 | 6/2005 | Anderson et al. |
| 2005/0142189 A1 | 6/2005 | Lambert et al. |
| 2005/0148534 A1 | 7/2005 | Castellino et al. |
| 2005/0152979 A1 | 7/2005 | Besman et al. |
| 2005/0187147 A1 | 8/2005 | Newman et al. |
| 2005/0232952 A1 | 10/2005 | Lambert et al. |
| 2005/0238634 A1 | 10/2005 | Broder et al. |
| 2005/0267201 A1 | 12/2005 | Gutierrez-Rocca et al. |
| 2005/0272806 A1 | 12/2005 | Falotico et al. |
| 2006/0003002 A1 | 1/2006 | Fikstad et al. |
| 2006/0003976 A1 | 1/2006 | Zhang et al. |
| 2006/0024360 A1 | 2/2006 | Chen |
| 2006/0172014 A1 | 8/2006 | Curd et al. |
| 2006/0188566 A1 | 8/2006 | Liversidge et al. |
| 2006/0189679 A1 | 8/2006 | Holton et al. |
| 2006/0223760 A1 | 10/2006 | Li et al. |
| 2006/0229359 A1 | 10/2006 | Zhang et al. |
| 2006/0234909 A1 | 10/2006 | Newman et al. |
| 2006/0263434 A1 | 11/2006 | Desai et al. |
| 2006/0292186 A1 | 12/2006 | Garrigue et al. |
| 2007/0060635 A1 | 3/2007 | Broder et al. |
| 2007/0082838 A1 | 4/2007 | De et al. |
| 2007/0116729 A1 | 5/2007 | Palepu et al. |
| 2007/0117744 A1 | 5/2007 | Desai et al. |
| 2007/0128289 A1 | 6/2007 | Zhao |
| 2007/0128290 A1 | 6/2007 | Desai et al. |
| 2007/0141093 A1 | 6/2007 | Zhang et al. |
| 2007/0166388 A1 | 7/2007 | Desai et al. |
| 2007/0207173 A1 | 9/2007 | Chen et al. |
| 2007/0207196 A1 | 9/2007 | Zhang |
| 2007/0208044 A1 | 9/2007 | Cai et al. |
| 2007/0244113 A1 | 10/2007 | Cai et al. |
| 2007/0244114 A1 | 10/2007 | Cai et al. |
| 2007/0249601 A1 | 10/2007 | Cai et al. |
| 2007/0281934 A1 | 12/2007 | Buggy et al. |
| 2008/0146651 A1 | 6/2008 | Jee et al. |
| 2008/0319048 A1 | 12/2008 | Palepu et al. |
| 2009/0215882 A1 | 8/2009 | Bouzada et al. |
| 2009/0215883 A1 | 8/2009 | Bouzada et al. |
| 2009/0227549 A1 | 9/2009 | Palepu et al. |
| 2009/0318543 A1 | 12/2009 | Vu et al. |
| 2010/0015195 A1 | 1/2010 | Jain et al. |

FOREIGN PATENT DOCUMENTS

| | | |
|---|---|---|
| WO | WO-99/24073 | 5/1999 |
| WO | WO-00/78247 | 12/2000 |
| WO | WO-01/72299 | 10/2001 |
| WO | WO-01/72300 | 10/2001 |
| WO | WO-02/26208 | 4/2002 |
| WO | WO-02/092077 | 11/2002 |
| WO | WO-03/057208 | 7/2003 |
| WO | WO-03/074027 | 9/2003 |
| WO | WO-2005/020962 | 3/2005 |
| WO | WO-2005/039554 | 5/2005 |
| WO | WO-2005/097105 | 10/2005 |
| WO | WO-2006/133510 | 12/2006 |
| WO | WO-2007/020085 | 2/2007 |
| WO | WO-2008/026048 | 8/2007 |
| WO | WO-2008/042841 | 4/2008 |
| WO | WO-2009/002425 | 12/2008 |
| WO | WO-2009/090614 | 7/2009 |

OTHER PUBLICATIONS

International Search Report and Written Opinion of the International Search Authority dated Sep. 3, 2008 in corresponding PCT/US2008/007619.

Eriox Product Literature, Nov. 2007.

Accelerated Examination Support Document filed on Mar. 11, 2010 for U.S. Appl. No. 12/721,563.

Decision on Petition to Make Special for New Application issued on Mar. 23, 2010 for U.S. Appl. No. 12/721,563.

Request for Reconsideration of Dismissal on Petition to Make Special for New Application filed on Apr. 23, 2010 for U.S. Appl. No. 12/721,563.

Decision on Petition to Make Special for New Application issued on May 5, 2010 for U.S. Appl. No. 12/721,563.

Non-final Office Action issued on May 18, 2010 for U.S. Appl. No. 12/721,563.

Interview Summary issued on Jun. 17, 2010 for U.S. Appl. No. 12/721,563.

Amendment and Response to Office Action and Record of Interview filed on Jun. 18, 2010 for U.S. Appl. No. 12/721,563.

Updated Accelerated Examination Support Document filed on Jun. 18, 2010 for U.S. Appl. No. 12/721,563.

Notice of Allowance issued on Jul. 1, 2010 for U.S. Appl. No. 12/721,563.

Record of Interview filed on Jul. 1, 2010 for U.S. Appl. No. 12/721,563.

* cited by examiner

DOCETAXEL FORMULATIONS WITH LIPOIC ACID

CROSS REFERENCE TO RELATED APPLICATIONS

This application is a continuation-in-part of U.S. patent application Ser. No. 12/721,564 ("'564 application"), filed on Mar. 11, 2010, now U.S. Pat. No. 8,746,310 which is a continuation-in-part of U.S. patent application Ser. No. 12/589,145 ("'145 application"), filed on Oct. 19, 2009 now U.S. Pat. No. 8,541,465. Both the '564 application and the '145 application are incorporated by reference.

FIELD OF THE INVENTION

The present invention relates to sterile pharmaceutical formulations comprising docetaxel, at least one solubilizer, TPGS, at least one hydrotrope, and α-lipoic acid, wherein the formulation is substantially free of polysorbates and polyethoxylated castor oil. The pharmaceutical formulations may require dilution with an infusion solution before administration to a patient in need thereof. Furthermore, the present invention relates to methods for administering docetaxel to patients in need thereof and for preparing the pharmaceutical formulations.

BACKGROUND OF THE INVENTION

Antineoplastic agents inhibit and combat the development of neoplasms, which are abnormal masses of tissue resulting from irregular proliferation of cells. One such antineoplastic agent is docetaxel, a taxane compound derived from the renewable needle biomass of yew plants. Docetaxel binds to free tubulin and promotes the assembly of microtubules, which reduces the availability of tubulin for, and thereby prevents, cell division. Simultaneously, docetaxel inhibits microtubule disassembly, causing apoptosis. See TAXOTERE® Prescribing Information.

Docetaxel is marketed as TAXOTERE®, which is FDA-approved for breast cancer, non-small cell lung cancer, hormone refractory prostate cancer, gastric adenocarcinoma, and squamous cell carcinoma of head and neck cancer. TAXOTERE is available as a sterile solution of docetaxel in a sealed vial, i.e., a single-vial injection concentrate, containing 20 mg/mL docetaxel; 0.54 g/mL polysorbate 80, and 0.395 g/mL dehydrated alcohol solution. For administration to patients, an amount of TAXOTERE injection concentrate is injected into a 250 mL infusion bag or bottle of either 0.9% sodium chloride solution or 5% dextrose solution to produce a final concentration of 0.3 to 0.74 mg/mL. The recommended therapy is six cycles of docetaxel given once every three weeks. See id.

The presence of polysorbate 80 in TAXOTERE, however, most often results in serious side effects. Such reactions characterized by generalized rash/erythema, hypotension and/or bronchospasm, or very rarely fatal anaphylaxis, have been reported in patients. Hypersensitivity reactions require immediate discontinuation of the TAXOTERE infusion and administration of appropriate therapy.

In order to reduce the side effects induced by polysorbate 80, patients are treated with dexamethasone for three days prior to therapy. Dexamethasone is a steroid that suppresses the immune response in patients, which can be especially detrimental in cancer patients under chemotherapy, whose immunity may already be compromised due to the destruction of healthy cells by the chemotherapeutic treatment. As a result, these patients can be susceptible to bacterial and fungal infections. Further, despite receiving the recommended 3-day dexamethasone premedication, patients still report hypersensitivity side effects from TAXOTERE.

Due to these side effects, most of the patients stop TAXOTERE therapy by the end of the second or third cycle, skip a dose, or continue further therapy at a reduced dose. Similarly, other solubilizing agents such as CREMOPHOR EL®, which is a polyethoxylated castor oil used in connection with the marketed paclitaxel product TAXOL®, induce similar allergic reactions requiring premedication with a steroid.

Therefore, a new single-vial docetaxel injection concentrate formulation is needed to avoid these side effects, premedication requirements, and patient noncompliance issues associated with the currently marketed formulation of TAXOTERE.

SUMMARY OF THE INVENTION

Applicant has developed stable docetaxel formulations of single-vial injection concentrates, which are liquids ready for dilution without any intermediate dilution steps; docetaxel final dilution for infusion (sometimes referred to as the final concentrate); and methods for administering docetaxel to patients in need thereof and for preparing the docetaxel formulations.

Therefore, an aspect of the invention may relate to a sterile pharmaceutical formulation for use in treatment of a patient in need thereof, such as a single-vial injection concentrate, comprising (a) docetaxel, or a pharmaceutically acceptable salt thereof; (b) glycofurol; (c) α-lipoic acid; (d) TPGS; (e) one or more hydrotropes; and (f) optionally one or more agents having a pKa of about 3 to about 6; wherein the formulation is substantially free of polysorbates and polyethoxylated castor oil.

In certain embodiments, the docetaxel, or pharmaceutically acceptable salt thereof, is in an amount of about 5 mg/mL to about 50 mg/mL. In some embodiments, the docetaxel, or a pharmaceutically acceptable salt thereof, is in an amount of about 10 mg/mL or about 20 mg/mL.

In certain embodiments, the α-lipoic acid, or pharmaceutically acceptable salt thereof, is in an amount of about 0.1 mg/mL to about 5 mg/mL. In some embodiments, the α-lipoic acid, or pharmaceutically acceptable salt thereof, is in an amount of about 0.625 mg/mL.

In further embodiments, the formulation comprises one or more agents having a pKa of about 3 to about 6. In some embodiments, the one or more agents having a $pK_a$ of about 3 to about 6 comprises a buffer or an acid. In certain embodiments, the acid is a weak acid. In particular embodiments, the weak acid is citric acid.

In some embodiments, the one or more hydrotropes is at least polyethylene glycol (PEG). In certain embodiments, the PEG is PEG 400.

In some embodiments, the formulation further comprises water for injection.

In embodiments of the invention, the formulation is ready to be combined with an infusion solution administration to the patient in need thereof. In certain embodiments, the formulation requires no further dilution before it is combined with an infusion solution for administration to the patient in need thereof.

In some embodiments, the formulation comprises an infusion solution. In certain embodiments, the infusion solution is selected from the group consisting of water for injection, 0.9% sodium chloride solution, or 5% dextrose solution. In further embodiments, the formulation comprising an infusion solution is ready for administration to a patient in need thereof.

Another aspect of the invention may relate to a sterile pharmaceutical formulation for use in treatment of a patient in need thereof, such as a single-vial injection concentrate, comprising (a) docetaxel, or a pharmaceutically acceptable salt thereof; (b) glycofurol; (c) α-lipoic acid; (d) TPGS; (e) citric acid; (f) water for injection; and (f) PEG 400; wherein the formulation is substantially free of polysorbates and polyethoxylated castor oil.

These and other embodiments are disclosed or are obvious from and encompassed by, the following Detailed Description.

DETAILED DESCRIPTION

The present invention is directed to formulations of single-vial docetaxel injection concentrate and docetaxel final dilution for infusion, and methods for administering docetaxel to patients in need thereof and for preparing the docetaxel formulations.

Docetaxel is classified as a taxane, a class of compounds that can eradicate cancer cells. This class of compounds is virtually insoluble in water, thereby making it difficult to formulate taxanes for intravenous administration to patients. Since taxanes are cytotoxic, these compounds must be diluted before administrating to patients. Thus, a formulator's challenge not only encompasses solubilizing the taxane, but also includes preventing the taxane from precipitating after it is diluted for intravenous ("IV") infusion and during administration into the patient's bloodstream. Due to such challenges, a formulator must select excipients that will solubilize the taxane and prevent it from precipitating upon subsequent dilution. Furthermore, these selected excipients must allow the taxane to be administered by the IV route to a patient safely and effectively, with minimal side effects. To this end, Applicant sought to develop a formulation that solubilized docetaxel, prevented its precipitation upon dilution, and avoided the use of polysorbates and polyethoxylated castor oil, which as described above most often induce side effects in patients and require premedication.

As a result, Applicant studied the solubility of docetaxel in several solvents as illustrated in Example 1. The results indicate that TPGS 1000, benzyl alcohol, acetic acid, ethanol, and glycofurol were comparable or superior to TWEEN 80® and TWEEN 20® with respect to solubilizing docetaxel.

Applicant then explored the stability of docetaxel when formulated as a single-vial injection concentrate, i.e., sterile liquids of docetaxel in a single vial, that is ready to add to an infusion solution, as seen in Examples 2 and 3. Single-vial injection concentrates were prepared and demonstrated stability after storage at 40° C. for up to 6, months, or after storage at 25° C. for up to 12 months.

Taken together, Applicant has developed a single-vial injection concentrate formulation that solubilizes docetaxel, prevents its precipitation upon dilution, and avoids the use of polysorbates and polyethoxylated castor oil associated with side effects requiring patient premedication.

DEFINITIONS

As used herein, "docetaxel" refers to a drug substance having the chemical name of (2R,3S)—N-carboxy-3-phenylisoserine, N-tert-butyl ester, 13-ester with 5β-20-epoxy-1,2α,4,7β,10β,13α-hexahydroxytax-11-en-9-one 4-acetate 2-benzoate, trihydrate. Docetaxel has the following structural formula:

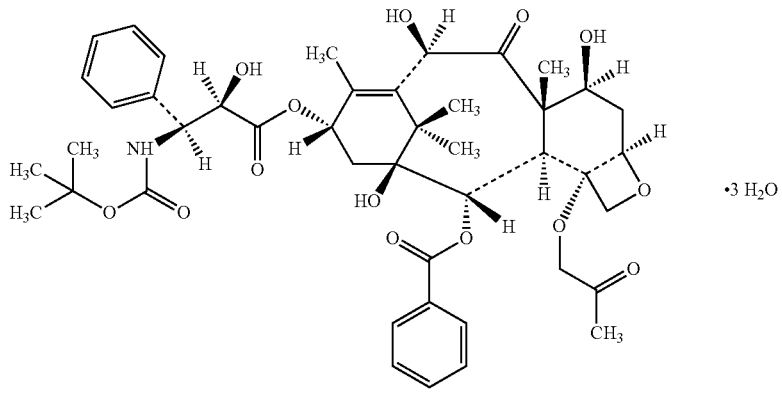

Docetaxel, as currently marketed by Sanofi-Aventis, is a white to almost-white powder with an empirical formula of $C_{43}H_{53}NO_{14} \cdot 3H_2O$, and a molecular weight, as a trihydrate, of 861.9.

As used herein, "single-vial injection concentrate" (sometimes referred to as "sterile liquid in a single vial") refers to a sterile liquid in a single vial that can be administered by IV to a patient upon dilution with an infusion solution, i.e., no other dilution may be necessary before dilution with the infusion solution.

"Final dilution for infusion" refers to the solution prepared by mixing the single-vial injection concentrate with an infusion solution.

"Infusion solution" refers to a solution to dilute the single-vial injection concentrate for administration to a patient.

As used herein, "solubilizer" refers to a solvent that is capable of dissolving docetaxel (or a pharmaceutically acceptable salt thereof) to prepare an injection concentrate. TWEEN 80®, glycofurol, benzyl alcohol and ethanol can be classified as solubilizers.

As used herein, "hydrotrope" refers to a material that can solubilize docetaxel or any such other lipophilic agent, if present in a sufficient quantity, and prevents the precipitation of docetaxel when the injection concentrate is further diluted to the initial diluted solution or final dilution for infusion. A hydrotrope does not dissolve the drug to the extent as the solubilizer. Two or more hydrotropes can act synergistically on solubility such that the combination can be used as a "solubilizer" in the context of the present invention. TPGS 1000, polyethylene glycol (PEG) 400, and propylene glycol (PG) are classified as hydrotropes, while 10% to 20% of ethanol can be used as a hydrotrope in combination with one or more hydrotropes.

As used herein, "substantially free" refers to the presence of a material in an amount less than about 5% (peak area %), or about 3%, or about 1%, or about 0.5%, or about 0.1%, or about 0% (i.e., totally free) as measured by HPLC with the UV detector set at a specific wavelength.

As used herein, "impurity" refers to any component of a drug product that is not the drug substance or an excipient in the drug product. See *ICH Guidelines: Impurities in New Drug Products* at 6. An impurity can include any degradant of a drug product.

As used herein, "unknown impurity" refers to an impurity of docetaxel other than 10-oxo-docetaxel, 7-hydroxy-epi-docetaxel, or 7-epi-10-oxo-docetaxel.

As used herein, "components" refers to parts of a whole. For example, components of the single-vial injection concentrate refers to the docetaxel, one or more solubilizers, etc., that make up the single-vial injection concentrate.

Docetaxel Formulations of Single-Vial Injection Concentrates

The present invention relates to formulations of single-vial docetaxel injection concentrates comprising docetaxel or a pharmaceutically acceptable salt thereof, one or more solubilizers, α-lipoic acid, TPGS, one or more hydrotropes; and optionally one or more agents having a $pK_a$ of about 3 to about 6. The formulations are substantially free of excipients that can cause severe side effects and maintains chemical stability during storage.

Docetaxel may be anhydrous or as a trihydrate, and may be present in the injection concentrate in an amount of about 2 mg/mL to about 40 mg/mL, or about 5 mg/mL to about 25 mg/mL, such as about 10 mg/mL or about 20 mg/mL. Stability as described above may be maintained in single-vial injection concentrates comprising docetaxel at concentrations other than about 2 mg/mL to about 40 mg/mL through particular concentrations of the other excipients.

Applicants have discovered that particular solubilizers may be used in formulations of single-vial docetaxel injection concentrates that do not induce severe side effects or do not likely require premedication with a steroid. If docetaxel is formulated without polyethoxylated castor oil or polysorbate 80, it should be better tolerated in cancer patients, thereby allowing these patients to take the medication for a longer period of time without dose interruption and/or reduction as compared to the current marketed formulation, i.e., TAXOTERE. For example, docetaxel, formulated without polyethoxylated castor oil or polysorbate 80 can likely be administered to cancer patients at much higher doses than TAXOTERE's dosing range of 75 to 100 mg/m², at higher infusion rates (up to at least 1 mg/mL in 10 to 15 minutes infusion time), for longer exposure to the drug (more than six cycles), and/or with less than three weeks between cycles.

Additionally, if docetaxel can be formulated without polyethoxylated castor oil or polysorbate 80, it is likely it can be administered to cancer patients without pre-medicating with steroids. The reduction or elimination of the steroid pretreatment phase can reduce concerns of immune system depression and other side effects, as well as of interactions with other drugs that the patient may be taking. Also, eliminating polysorbates in the formulation can remove the risk of skin rashes, edema, hypotension and bradycardia.

The solubilizers of the present invention include, but are not limited to, acetic acid, benzyl alcohol, ethanol, and glycofurol. Glycofurol is also known as tetrahydrofurfuryl alcohol polyethylene glycol ether and has the following structure:

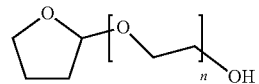

where n is on average 2, such as glycofurol 75, but may be other integers such as n=1. Glycofurol may be combined with a liquid PEG, such as PEG 200 or PEG 400. The resulting mixture may comprise glycofurol and PEG in a ratio % of about 15:85 to about 85:15, or about 30:70 to about 70:30, or about 50:50.

Ethanol is another solubilizer that can be used in the injection concentrate, as docetaxel is highly soluble in ethanol (120 mg/mL).

The solubilizer in the single-vial injection concentrate may be in an amount to comprise about 5% to about 20%, or about 10% to about 15%, of the total volume of the single-vial injection concentrate.

Hydrotropes used in the single-vial injection concentrate may include, but is not limited to, PEG such as PEG 300, 400 and 800; propylene glycol (PG); 50% PEG 400/50% PG; LUTROL® (as known as SOLUTOL®) 2% in PEG; tocopherol compounds; and acetic acid. Hydrotropes may be in the single-vial injection concentrate in an amount to q.s. the single-vial injection concentrate to its final volume.

The TPGS may be in the single-vial injection concentrate in an amount of about 100 mg/mL to about 250 mg/mL, or about 150 mg/mL to about 200 mg/mL, such as about 187.5 mg/mL.

The one or more agents having a $pK_a$ of about 3 to about 6 may be an acid, such as a weak acid, or a buffer. Weak acids for use in the present invention include, but are not limited to citric, acetic, ascorbic, benzoic, lactic, oxalic, propanic, and uric.

The buffer may comprise organic buffer materials that include, without limitation, the following materials together with their conjugate salts (which free compound/salt conjugate may form in situ from either the free compound or the conjugate salt being added alone as known in the art of buffer materials): citric acid, tartaric acid, b-alanine, lactic acid, aspartic acid, g-aminobutyric, succinic acid, oxalic acid, e-aminocaproic acid, acetic acid, propionic acid, and malonic acid.

The one or more agents having a pKa of about 3 to 6 may be in an amount of about 0.5 mg/mL to about 8 mg/mL, or about 3 mg/mL to about 5 mg/mL, such as about 4 mg/mL.

α-lipoic acid may be in the single-vial injection concentrate in an amount of about 0.3 mg/mL to about 1 mg/mL, or about 0.5 mg/mL to about 0.7 mg/mL, such as about 0.625 mg/mL.

The single-vial concentrate may further comprise an antioxidizing agent. Antioxidizing agents of the present invention may include, but are not limited to, dihydrolipoic acid, butylated hydroxyanisole ("BHA"), butylated hydroxytoluene ("BHT"), acetylcysteine, ascorbyl palmitate, monothioglycerol, potassium nitrate, sodium ascorbate, sodium formaldehyde sulfoxylate, sodium metabisulfite, sodium bisulfite, vitamin E or a derivative thereof, propyl gallate, edetate ("EDTA") (e.g., disodium edetate), diethylenetriaminepentaacetic acid ("DTPA"), triglycollamate ("NT"), or a combination thereof.

In addition, the single-vial injection concentrate may further comprise water, such as water for injection. The amount of water may be about 10% to 20% of the total volume, or about 15% to about 17.5% of the total volume, such as about 16.25% of the total volume.

In certain embodiments, the single-vial injection concentrate may comprise the components shown in Table 1.

TABLE 1

Single-vial injection concentrate according to certain embodiments.

| Component | Quantity (by volume) | Quantity (by weight) |
|---|---|---|
| Docetaxel | 10 mg | 10 mg |
| Glycofurol | 0.125 mL | 135.6 mg |
| α-lipoic acid | 0.625 mg | 0.625 mg |
| TPGS 1000 | 187.5 mg | 187.5 mg |
| Water | 0.1625 mL | 162.5 mg |
| Citric acid | 4 mg | 4 mg |
| PEG 400 | q.s. to 1 mL | q.s. to 1 mL |

Regarding the components of the single-vial injection concentrate, one of ordinary skill in the art can convert between quantities of the components expressed in units of volume, and quantities of the components expressed in units of weight. For example, the skilled artisan can recognize that water for injection expressed as 1 mL is equivalent to water for injection expressed as 1 g.

The single-vial injection concentrate may be substantially free of polysorbate 80, CREMOPHOR®, and/or all polyethoxylated vegetable oils (whether totally hydrogenated, partially hydrogenated, or not hydrogenated). In addition, the single-vial injection concentrate may be substantially free of hydroxyalkyl substituted cellulosic polymers.

The single-vial injection concentrate may be stored at room temperature (about 15° C. to about 30° C.) or under refrigerated conditions (about 2° C. to about 8° C.). The injection concentrate can be stored for up to about two years, preferably from about one year to about one and half years, at room temperature and longer still under refrigeration.

Formulation of a Final Dilution for Infusion

The present invention also relates to the formulation of a docetaxel final dilution for infusion comprising the single-vial injection concentrate mixed with an infusion solution. Infusion solutions in the final dilution for infusion may include, but are not limited to, water for injection, 0.9% sodium chloride solution (or normal saline), 5% dextrose solution, or the like. The final dilution for infusion may be appropriate for injection into patients.

The final dilution for infusion may comprise docetaxel having a concentration of about 0.32 mg/mL to about 0.74 mg/mL. Therefore, the single-vial for infusion may be added to the appropriate amount of the infusion solution, which may be dependent on the concentration of docetaxel in the single-vial injection concentrate. For example, if the single-vial injection concentrate contains 10 mg/mL of docetaxel, preparation of the final dilution for infusion would involve mixing 1 mL of the single-vial injection concentrate with infusion solution of about 30.25 mL or about 12.51 mL to result in a final dilution for infusion having a docetaxel concentration of about 0.32 mg/mL or about 0.74 mg/mL, respectively.

The final dilution for infusion can be stored at room temperature for at least about 8 hours, as these conditions generate no detectable levels of impurities. In addition, after storage at room temperature for up to 8 hours, the final dilution for infusion will be clear and colorless. Moreover, the potency of the docetaxel in the final dilution for infusion will remain greater than at least 98%.

Methods of Preparing Docetaxel for Administration to a Patient in Need Thereof

The present invention relates to a method of preparing the single-vial injection concentrates. The method may comprise mixing docetaxel or a pharmaceutically acceptable salt thereof, one or more solubilizers, one or more hydrotropes, TPGS, one or more agents having a $pK_a$ of about 3 to about 6, and α-lipoic acid. The volume of the single-vial injection concentrate may then be adjusted by adding more of the solubilizer(s) or the hydrotrope(s).

The addition of these components of the single-vial injection concentrate can be achieved by methods known in the art. For example, one or more of the components may be added to each other and then mixed in a common receptacle, or the components may be added to a common receptacle in a particular order, or the components may be added to a common receptacle simultaneously. In certain embodiments, the docetaxel and the solubilizer are combined separately from the other components. In some embodiments, the docetaxel is dissolved in the solubilizer separately from the other components.

The components of the single-vial injection concentrates may be mixed by methods known in the art. For example, the components can be mixed by simple mixing, or may be mixed with a mixing device continuously, periodically, or a combination thereof. Mixing devices may include, but are not limited to, a magnetic stirrer, shaker, a paddle mixer, homogenizer, and any combination thereof.

The addition and mixing of one or more components of the single-vial and injection concentrates may occur under controlled conditions. For example, the addition and mixing of the components may occur under conditions such as under nitrogen, at a particular temperature, or at a particular humidity, etc., or the adding and mixing may occur under certain temperatures. In certain embodiments, the adding and mixing may occur under temperature conditions of about 25° C. to about 80° C. Additionally, the addition and mixing may be under controlled light exposure, such as in yellow light or under protection from direct exposure to light.

After the single-vial injection concentrate is prepared, it may be sterilized by methods known in the art. The single-vial injection concentrate may undergo aseptic filtration (e.g., using a 0.2 μm disposable membrane filter).

Dissolved gases, such as nitrogen or oxygen, may be removed form the single-vial injection concentrate using methods known in the art. For example, gases may be removed through sparging with nitrogen or argon and have a nitrogen overlay prior to stoppering and crimping.

Additionally, the injection concentrate may be placed into a container (e.g. an intravenous solution bag, bottle, vial, ampoule, or pre-filled sterile syringe). The container may have a sterile access port for piercing by a hypodermic injection needle. In some embodiments, the single-vial injection concentrate may be filled in one or more pre-sterilized depyrogeneated vials and stopped aseptically with a pre-sterilized butyl stopper.

The single-vial injection concentrate may undergo final dilution with an infusion solution. The infusion solution may include, but is not limited to, normal saline, 5% dextrose, water for injection, or other suitable injection diluents for administration to the patient, to form a final dilution for infusion.

As the present invention is directed to delivery of docetaxel, once diluted to appropriate injection (especially infusion, most particularly IV infusion) concentrations, it may be administered in appropriate amounts for treating docetaxel responsive conditions known in the art. In addition, the present invention permits administration of higher doses and concentrations of docetaxel than the currently marketed TAXOTERE®. As such, the concentrates and administrable dosage forms thereof made from the present invention are also useful to treat docetaxel-responsive indications known in the art for which the current marketed TAXOTERE® formulation is not recommended because of an inability to administer docetaxel at a sufficiently high dose, either acutely or cumulatively. These include, without limitation, carcinomas such as colorectal, prostate, pancreatic, renal, and liquid tumors like lymphoma and leukemia.

Administration of the docetaxel final dilution for infusion to the patient may not require premedication with a steroid. Antihistamines are likely not required as a pretreatment but may be administered to the patient as a precaution.

Methods of Administering Docetaxel Formulations

The present invention relates to methods of administering formulations described herein, in particular the final dilutions for infusion. In certain embodiments, the final dilution for infusion is administered by IV as a one-hour infusion at room temperature to patients in need thereof.

In some embodiments, an in-line filter is used during administration. In particular embodiments, the filter is of 0.22 µM nominal pore size.

The invention will now be further described by way of the following non-limiting examples, which further illustrate the invention; such examples are not intended, nor should they be interpreted, to limit the scope of the invention.

EXAMPLES

Example 1

In consideration of the severe side effects associated with the use of polysorbates, such as TWEEN 80®, as solubilizers of docetaxel, solubility studies were conducted to determine non-toxic solvents that can effectively dissolve docetaxel.

Solubility of docetaxel was assessed using several different solvents that are well-tolerated in subjects, as well as polysorbates for comparison. The solubility data for these solvents are summarized in Table 2.

TABLE 2

Solubility of Docetaxel in Various Solvents

| Solvents | Concentration (mg/mL) |
|---|---|
| TWEEN 80 ®* | 60 |
| TWEEN 20 ®* | 90 |
| PEG 400 | 10 |
| Propylene Glycol | 10 |
| 50% PEG 400/50% PG | 15 |
| 2% Lutrol in PEG 400 | 15 |
| Glycerol | 1.65 |
| Span 80 | 3.5 |
| TPGS 1000 | 50 |
| LABROFAC ™ (Capric triglyceride PEG 4 ester Macrogol 200) | 35 |
| PECEOL ® (Glycerol mono Oleate 40) | 7 |
| MAISINE ™ 35-1 (Glycerol mono linoleate) | 10 |
| Ethanol | 120 |
| N-Methyl 2-Pyrrolidone | 17.6 |
| Benzyl alcohol | 90 |
| Benzyl benzoate | 13 |
| Acetic acid | 60 |
| l-lactic acid | 6 |
| Glycofurol | 200 |

*polysorbates were included for comparison

The results indicate that TPGS 1000, benzyl alcohol, acetic acid, ethanol and glycofurol were comparable or superior to TWEEN 80® and TWEEN 20® with respect to solubilizing docetaxel. Docetaxel was most soluble in glycofurol.

Example 2

Docetaxel single-vial injection concentrates are prepared that are sterile liquids ready to be combined with an infusion solution for administration to patients in need thereof. Such single-vial injection concentrates are shown in Table 3.

TABLE 3

Docetaxel single-vial injection concentrates.

| Component | Quantity |
|---|---|
| Docetaxel | 80-120 mg |
| Glycofurol | 1-1.5 mL |
| TPGS 1000 | 1.5-2 mg |
| α-lipoic acid | 5-8 mg |
| Water | 1.25-2 mL |
| Citric acid | 20-60 mg |
| PEG 400 | q.s. to 10 mL |

Example 3

To determine the stability of a single-vial docetaxel injection concentrate according to certain embodiments of the invention, a single-vial docetaxel injection concentrate comprising the components shown in Table 4 was prepared.

TABLE 4

Components of the single-vial injection concentrate.

| Component | Quantity |
|---|---|
| Docetaxel | 100 mg |
| Glycofurol | 1.25 mL |
| TPGS 1000 | 1.875 mg |
| α-lipoic acid | 6.25 mg |
| Water | 1.625 mL |
| Citric acid | 40 mg |
| PEG 400 | q.s. to 10 mL |

The concentrate was sparged with nitrogen and stored in 15 mL vials. The vials were stored in either an upright position or an inverted position at either 40° C. or 25° C., for up to 9 months.

Stability, as characterized by the impurities that were present, was determined using high performance liquid chromatography (HPLC).

The stability results for the vials stored in an upright position and the vials stored in an inverted position are provided in Tables 5 and 6, respectively.

TABLE 5

Stability of single-vial injection concentrate stored in an upright position.

| Storage Temp. | Time Period | % of Initial | Total Peak Area % of Impurities |
|---|---|---|---|
| | Docetaxel API | | 0.11 |
| | Initial | 100 | 0 |
| 40° C. | 1 month | 99.9 | 0 |
| | 2 months | 99.8 | 0.07 |
| | 3 months | 99.8 | 0.17 |
| | 6 months | 99.8 | 0.40 |

TABLE 5-continued

Stability of single-vial injection concentrate stored in an upright position.

| Storage Temp. | Time Period | % of Initial | Total Peak Area % of Impurities |
|---|---|---|---|
| 25° C. | 3 months | 100 | 0 |
| | 6 months | 100 | 0.11 |
| | 9 months | 100 | 0.11 |

TABLE 6

Stability of single-vial injection concentrate stored in an inverted position.

| Storage Temp. | Time Period | % of Initial | Total Peak Area % of Impurities |
|---|---|---|---|
| | Docetaxel API | | 0.11 |
| | Initial | 100 | 0 |
| 40° C. | 1 month | 100 | 0 |
| | 2 months | 100 | 0.07 |
| | 3 months | 99.9 | 0.17 |
| | 6 months | 99.9 | 0.49 |
| 25° C. | 3 months | 100 | 0 |
| | 6 months | 100 | 0.11 |
| | 9 months | 100 | 0.14 |

The results indicate that the single-vial injection concentrates were stable. The % of initial concentrate was at least 99% and the total peak area % of impurities was below 0.50% for all tested storage conditions, including after storage at 40° C. for 6 months. In addition, the position of the vial did not affect the stability results.

Example 4

To determine the stability of the TPGS component of a single-vial docetaxel injection concentrate of the invention, additional studies were performed. A single-vial injection concentrate comprising the components shown in Table 7 was prepared.

TABLE 7

Components of the single-vial injection concentrate.

| Component | Quantity |
|---|---|
| Docetaxel | 100 mg |
| Glycofurol | 1.25 mL |
| TPGS 1000 | 1.875 mg |
| α-lipoic acid | 6.25 mg |
| Water | 1.625 mL |
| Citric acid | 40 mg |
| PEG 400 | q.s. to 10 mL |

The concentrate with sparged with nitrogen and stored in 15 mL vials. The vials were stored in either an upright position or an inverted position at either 40° C. or 25° C., for up to 12 months.

Stability, characterized by the presence of degradants, was assessed using HPLC. The stability results for the vials stored in an upright position and the vial stored in an inverted position are provided in Tables 8 and 9, respectively.

TABLE 8

Stability of single-vial injection concentrate stored in an upright position.

| Storage Temp. | Time Period | % of Initial | Total Peak Area % of Impurities |
|---|---|---|---|
| | Docetaxel API | | 0.11 |
| | Initial | 100 | 0 |
| 40° C. | 1 month | 100 | 0 |
| | 2 months | 100 | 0.08 |
| | 3 months | 99.0 | 0.27 |
| | 6 months | 99.0 | 0.45 |
| 25° C. | 3 months | 100 | 0 |
| | 6 months | 100 | 0.08 |
| | 9 months | 100 | 0.06 |
| | 12 months | 100 | 0.18 |

TABLE 9

Stability of single-vial injection concentrate stored in an inverted position.

| Storage Temp. | Time Period | % of Initial | Total Peak Area % of Impurities |
|---|---|---|---|
| | Docetaxel API | | 0.11 |
| | Initial | 100 | 0 |
| 40° C. | 1 month | 100 | 0.05 |
| | 2 months | 100 | 0.07 |
| | 3 months | 99.0 | 0.32 |
| | 6 months | 99.9 | 0.49 |
| 25° C. | 3 months | 100 | 0 |
| | 6 months | 100 | 0.08 |
| | 9 months | 100 | 0.11 |
| | 12 months | 100 | 0.17 |

These stability results were consistent with those obtain in the study of Example 3. The % of initial concentrate was at least 99% and the total peak area % of impurities was below 0.50% for all tested storage conditions, including after storage at 40° C. for 6 months and at 25° C. for 12 months. In addition, the position of the vial did not affect the stability results.

The stability of the TPGS component in particular was also assessed in the single-vial concentrates stored in vials in the upright position at 40° C. or 25° C., for up to 12 months using HPLC. The results are shown in Table 10.

TABLE 10

Stability of the TPGS component in a single-vial injection concentrate.

| Storage Temp. | Time Period | % of Initial for Total TPGS |
|---|---|---|
| | Initial | 100 |
| 40° C. | 1 month | 99.4 |
| | 2 months | 100.0 |
| | 3 months | 101.2 |
| | 6 months | 101.0 |
| 25° C. | 3 months | 100.0 |
| | 6 months | 100.0 |
| | 9 months | N/A (insufficient vials) |
| | 12 months | 98.7 |

These results indicate that the TPGS component of the single-vial injection concentrate was stable during storage for at least 9 months at up to at 40° C., and for at least 12 months at 25° C.

While specific embodiments of the subject invention have been discussed, the above specification is illustrative and not restrictive. One skilled in the art will appreciate that numerous changes and modifications can be made to the invention, and that such changes and modifications can be made without departing from the spirit and scope of the invention.

What is claimed is:

1. A sterile pharmaceutical formulation for use in treatment of a patient in need thereof, comprising:
   (a) docetaxel, or a pharmaceutically acceptable salt thereof;
   (b) a solubilizer selected from the group consisting of ethanol, glycofurol, and mixtures thereof;
   (c) d-alpha-tocopheryl polyethylene glycol 1000 succinate (TPGS 1000);
   (d) one or more hydrotropes, wherein the one or more hydrotropes are selected from the group consisting of polyethylene glycol, propylene glycol, acetic acid, and a combination thereof;
   (e) one or more agents having a $pK_a$ of about 3 to about 6, wherein the one or more agents comprise weak acids or salts thereof, or buffers; and
   (f) α-lipoic acid, or a pharmaceutically acceptable salt thereof, in an amount of about 0.1 mg/mL to about 5 mg/mL;
   wherein the formulation is substantially free of polysorbates and polyethoxylated castor oil.

2. The formulation of claim 1, wherein the docetaxel, or a pharmaceutically acceptable salt thereof, is in an amount of about 5 mg/mL to about 50 mg/mL.

3. The formulation of claim 2, wherein the docetaxel, or a pharmaceutically acceptable salt thereof, is in an amount of about 10 mg/mL to about 20 mg/mL.

4. The formulation of claim 1, wherein the α-lipoic acid, or a pharmaceutically acceptable salt thereof, is in an amount of about 0.625 mg/mL.

5. The formulation of claim 1, wherein the TPGS 1000 is in an amount of about 150 mg/mL to about 200 mg/mL.

6. The formulation of claim 5, wherein the TPGS 1000 is in an amount of about 187.5 mg/mL.

7. The formulation of claim 1, wherein the one or more agents having a $pK_a$ of about 3 to about 6 comprises citric acid.

8. The formulation of claim 1, wherein the one or more hydrotropes comprises polyethylene glycol (PEG), propylene glycol, or a mixture thereof.

9. The formulation of claim 8, wherein the PEG is PEG 400.

10. The formulation of claim 1, wherein the formulation further comprises water for injection.

11. The formulation of claim 1, wherein the formulation is sealed in a pre-sterilized depyrogeneated vial.

12. The formulation of claim 1, wherein the formulation requires no further dilution before it is combined with an infusion solution for administration to the patient in need thereof.

13. The pharmaceutical formulation of claim 1, further comprising an infusion solution.

14. The pharmaceutical formulation of claim 13, wherein the infusion solution is selected from the group consisting of water for injection, 0.9% sodium chloride solution, and 5% dextrose solution.

15. The pharmaceutical formulation of claim 13, wherein the formulation is ready for administration to a patient in need thereof.

16. A sterile pharmaceutical formulation for use in treatment of a patient in need thereof, comprising:
   (a) docetaxel, or a pharmaceutically acceptable salt thereof;
   (b) glycofurol;
   (c) α-lipoic acid, in an amount of about 0.1 mg/mL to about 5 mg/mL;
   (d) d-alpha-tocopheryl polyethylene glycol 1000 succinate;
   (e) citric acid;
   (f) water for injection; and
   (g) PEG 400;
   wherein the formulation is substantially free of polysorbates and polyethoxylated castor oil.

17. A sterile pharmaceutical formulation for use in treatment of a patient in need thereof, comprising:
   (a) docetaxel, or a pharmaceutically acceptable salt thereof;
   (b) ethanol;
   (c) α-lipoic acid, in an amount of about 0.1 mg/mL to about 5 mg/mL;
   (d) d-alpha-tocopheryl polyethylene glycol 1000 succinate;
   (e) citric acid;
   (f) water for injection; and
   (g) PEG 400;
   wherein the formulation is substantially free of polysorbates and polyethoxylated castor oil.

18. The pharmaceutical formulation of claim 1, further comprising an antioxidizing agent.

19. The pharmaceutical formulation of claim 18, wherein the antioxidizing agent comprises monothioglycerol.

20. A method of treating cancer comprising administering the pharmaceutical formulation of claim 13 to a patient in need thereof.

* * * * *